United States Patent [19]
Treppendahl

[11] Patent Number: 5,925,771
[45] Date of Patent: Jul. 20, 1999

[54] PROCESS FOR THE PREPARATION OF (−)-3,4-TRANS-DIARYLCHROMANS

[75] Inventor: Svend Treppendahl, Virum, Denmark

[73] Assignee: Novo Nordisk A/S, Bagsvaerd, Denmark

[21] Appl. No.: 08/957,823

[22] Filed: Oct. 27, 1997

Related U.S. Application Data

[60] Provisional application No. 60/031,247, Nov. 12, 1996.

[30] Foreign Application Priority Data

Oct. 28, 1996 [DK] Denmark ................................. 1194/96
Sep. 26, 1997 [DK] Denmark ................................. 1108/97

[51] Int. Cl.$^6$ ...................... C07D 311/58; C07D 405/12
[52] U.S. Cl. ............................................ 548/525; 549/406
[58] Field of Search ............................. 548/525; 549/406

[56] References Cited

U.S. PATENT DOCUMENTS 3,340,276  9/1967  Carney et al. ........................... 549/406
4,447,622  5/1984  Salman et al. ........................... 548/525

OTHER PUBLICATIONS

Saeed et al., Chemical Abstracts, 102:40068, 1985.
Salman et al., J. Med. Chem., 26, pp. 592–595, (1983).
Ray et al., J. Med. Chem., vol. 19, No. 2, pp. 276–279, (1976).

*Primary Examiner*—Fiona T. Powers
*Attorney, Agent, or Firm*—Steve T. Zelson; Elias J. Lambiris; Carol E. Rozek

[57] ABSTRACT

Disclosed is a process for preparing (−)-3,4-trans-diarylchromans of formula I

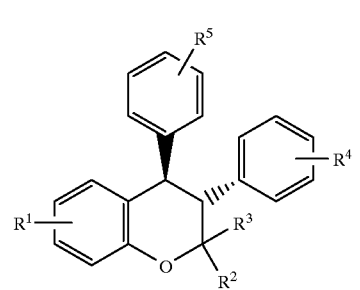

(I)

wherein $R^1$, $R^2$, $R^3$, $R^4$ and $R^5$ are as defined in the specification. This process involves reacting a (+,−)-3,4-cis-diarylchroman with a chiral acid in an inert organic solvent to obtain the chiral acid salt of the (−)-3,4-cis enantiomer in crystalline form, subjecting the crystalline salt to hydrolysis, and rearranging the (−)-3,4-cis enantiomer to the (−)-3,4-trans enantiomer with a strong base in an inert aprotic solvent.

21 Claims, No Drawings

PROCESS FOR THE PREPARATION OF (−)-3,4-TRANS-DIARYLCHROMANS

CROSS-REFERENCE TO RELATED APPLICATIONS

This application claims priority under 35 U.S.C. 119 of United States provisional application Ser. No. 60/031,247 filed on Nov. 12, 1996 and Danish application serial nos. 1194/96 filed Oct. 28, 1996 and 1108/97 filed on Sep. 26, 1997, the contents of which are fully incorporated herein by reference.

FIELD OF INVENTION

The present invention relates to a novel and advantageous process for the preparation of (−)-3,4-trans-diarylchromans of the following formula I:

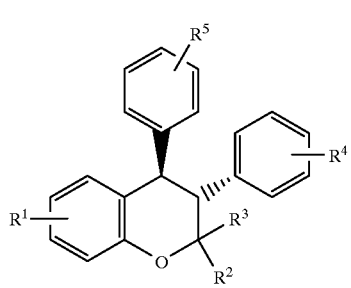

(I)

wherein $R^1$, $R^4$ and $R^5$ are individually hydrogen, hydroxy, halogen, trifluoromethyl, $C_{1-6}$alkyl, $C_{1-6}$alkoxy or —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6- membered heterocyclic group containing one or two heteroatom(s) which heterocyclic group is optionally substituted with $C_{1-6}$alkyl; and $R^2$ and $R^3$ are individually hydrogen or $C_{1-6}$alkyl; and salts thereof.

The present invention provides a process which comprises reacting a (+,−)-3,4-cis-diarylchroman with a chiral acid, e.g. (−)-di-p-toluoyltartaric acid, in an inert organic solvent to obtain the chiral acid salt, e.g. (−)-di-p-toluoyltartaric acid salt, of the (−)-3,4-cis enantiomer in crystalline form, subjecting the crystalline salt to hydrolysis and rearranging the (−)-3,4-cis enantiomer to the (−)-3,4-trans enantiomer with a strong base in an inert aprotic solvent.

The present invention also relates to novel intermediates of formula III

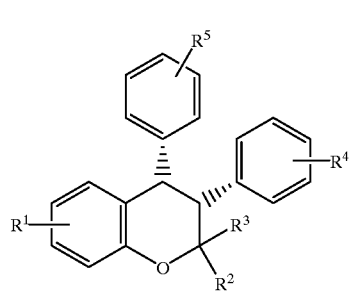

(III)

wherein $R^1$, $R^2$, $R^3$, $R^4$ and $R^5$ are as defined above; or a salt thereof, useful in the preparation of the compounds of formula I.

BACKGROUND OF THE INVENTION

U.S. Pat. No. 5,280,040 discloses a class of 3,4-diarylchromans and their salts useful in the treatment of bone loss due to osteoporosis or other conditions. Furthermore, PCT/DK96/00014 discloses that these compounds are useful in the treatment of hyperlipoproteinaemia, hypertriglyceridaemia, hyperlipidaemia, or hypercholesterolaemia or arteriosclerosis or for anticoagulative treatment. PCT/DK96/00015 discloses that these compounds are useful in the treatment of gynaecological disorders, such as endometriosis, dysfunctional bleedings, endometrial cancer, polycystic ovarian syndrome and anovulatoric bleeding and for the induction of endometrial thinning. The compounds are also known to have useful effects on gynaecomastia, obesity, vasodilation (respectively from PCT/DK96/00012, PCT/DK96/00011, and PCT/DK96/00013) and furthermore on e.g. Alzheimers disease (PCT/DK96/00010).

A process for the preparation of (+,−)-3,4-trans diarylchromanes is described in U.S. Pat. No. 3,822,287 and by Suprabhat Ray et al. in J. Med. Chem.19,276 (1976). The (+,−)-3,4-transisomer is obtained by conversion of the (+,−)-3,4-cis-isomer by means of an organometallic base-catalyzed rearrangement as described in US Patent Specification No. 3,822,287.

The resolution of (+,−)-3,4-trans-7-methoxy-2,2-dimethyl-3-phenyl-4-{4-[2-(pyrrolidin-1-yl)ethoxy] phenyl}chromane in its optical antipodes is described in U.S. Pat. No. 4,447,622. According to this process the (+,−)-3,4-trans-7-methoxy-2,2-dimethyl-3-phenyl-4-{4-[2 (pyrrolidin-1-yl)ethoxy]phenyl}chromane is reacted with di-p-tolyl-l-tartaric acid monohydrate in a protic solvent, the reaction mixture is subjected to fractional crystallization and the crystalline salt is subjected to alkaline hydrolysis to produce the desired enantiomer.

Example 1 of U.S. Pat. No. 4,447,622 describes the preparation of the (−)-3,4-trans enantiomer, shown by the following formula:

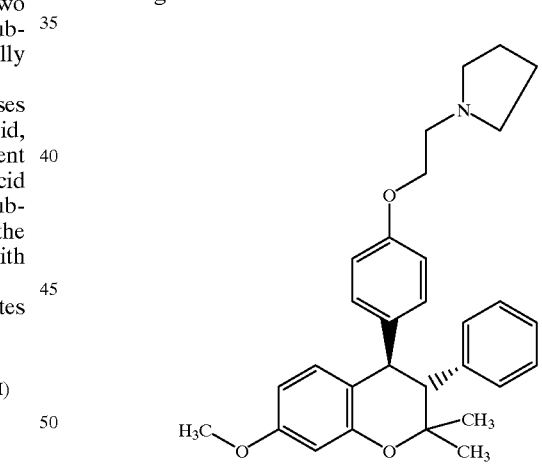

When using the process disclosed in U.S. Pat. No. 4,447,622 the desired (−)-3,4-trans enantiomer is only obtained with a low chiral purity, less than 80% ee (enantiomeric excess) after the first crystallization. In order to improve the chiral purity the enantiomer has to be crystallized several times.

One object of the present invention is therefore to provide a new and improved process for the preparation of (−)-3,4-trans enantiomers of compounds of formula I which process is adaptable to large scale manufacture, provide good yields and high purity and reduce the cost of manufacture.

Another object of the present invention is to provide a new intermediate of formula III, which is useful in the preparation of compounds of formula I.

DESCRIPTION OF THIS INVENTION

The process of the invention for the preparation of a (−)-3,4-trans-compound of formula I

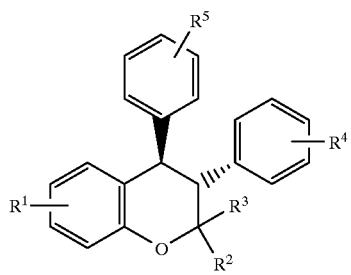

wherein $R^1$, $R^4$ and $R^5$ are individually hydrogen, hydroxy, halogen, trifluoromethyl, $C_{1-6}$alkyl, $C_{1-6}$alkoxy or —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6- membered heterocyclic group containing one or two heteroatom(s) which heterocyclic group is optionally substituted with $C_{1-6}$alkyl; and $R^2$ and $R^3$ are individually hydrogen or $C_{1-6}$alkyl; or a salt thereof, comprises treating a cis-racemate of a compound of formula II

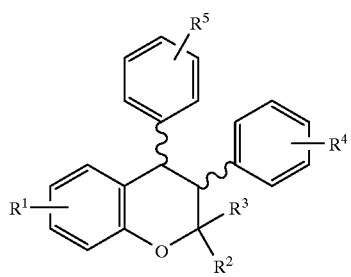

wherein $R^1$, $R^2$, $R^3$, $R^4$ and $R^5$ are as defined above or a salt thereof with a chiral acid in an inert organic solvent, crystallizing the chiral acid salt of the (−)-3,4-cis enantiomer, hydrolyzing the optically active acid salt and rearranging the resulting (−)-3,4-cis enantiomer to the corresponding (−)-3,4-trans enantiomer of above formula I by treatment with a strong base in an aprotic solvent and optionally forming a salt thereof.

In a preferred embodiment the process of the invention for the preparation of a (−)-3,4-trans-compound of formula I

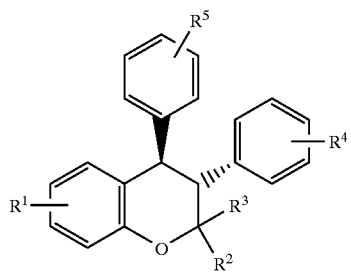

wherein $R^1$, $R^4$ and $R^5$ are individually hydrogen, hydroxy, halogen, trifluoromethyl, $C_{1-6}$alkyl, $C_{1-6}$alkoxy or —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6- membered heterocyclic group containing one or two heteroatom(s) which heterocyclic group is optionally substituted with $C_{1-6}$alkyl; and $R^2$ and $R^3$ are individually hydrogen or $C_{1-6}$alkyl, or a salt thereof, comprises treating a cis-racemate of a compound of formula II

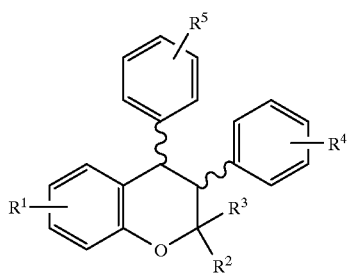

wherein $R^1$, $R^2$, $R^3$, $R^4$ and $R^5$ are as defined above or a salt thereof with (−)-di-p-toluoyltartaric acid in an inert organic solvent, crystallizing the (−)-di-p-toluoyltartaric acid salt of the (−)-3,4-cis enantiomer of formula III

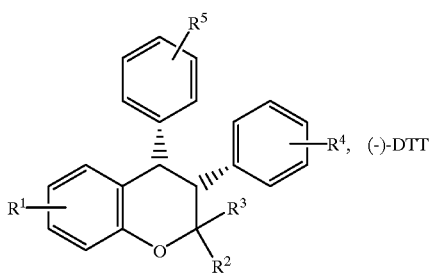

wherein $R^1$, $R^2$, $R^3$, $R^4$ and $R^5$ are as defined above, hydrolyzing the optically active acid salt and rearranging the resulting (−)-3,4-cis enantiomer to the corresponding (−)-3, 4-trans enantiomer of above formula I by treatment with a strong base in an aprotic solvent and optionally forming a salt thereof.

Furthermore, the invention relates to intermediate compounds of formula III

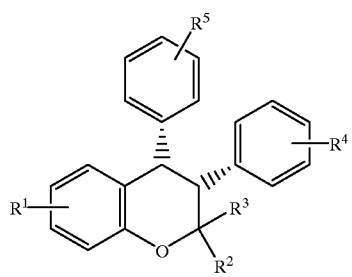

wherein $R^1$, $R^2$, $R^3$, $R^4$ and $R^5$ are as defined above; and salts thereof. Intermediates of formula III are useful for preparing the compounds of formula I, and moreover, some of these compounds of formula III possess the same pharmaceutical activity as compounds of formula I.

A preferred embodiment of the compound of formula III is the (−)-di-p-toluoyltartaric acid salt having the formula

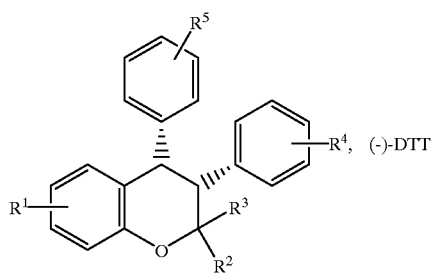

(III)

Preferred Intermediates of formula III of the invention include those in which $R^1$ is hydroxy or $C_{1-6}$alkoxy, especially methoxy. Furthermore, $R^2$ and $R^3$ preferably are the same and $Cl_{1-6}$alkyl, especially methyl; $R^4$ is preferably hydrogen; and $R^5$ is preferably —O—$(CH_2)_n$—$NR^6R^7$ wherein n is 2 and $R^6$ and $R^7$ together with the N atom is a saturated or unsaturated 5- or 6- membered heterocyclic group containing one or two heteroatom(s) and optionally substituted with $C_{1-6}$alkyl. Within particularly preferred embodiments, $R^1$ is in the 7-position and is hydroxy or $C_{1-6}$alkoxy, particularly methoxy; each of $R^2$ and $R^3$ is methyl, $R^4$ is hydrogen, and $R^5$ is in the 4-position and is 2-(pyrrolidin-1-yl)ethoxy.

A preferred embodiment of the intermediate of formula III is 3,4-cis-7-methoxy-2,2-dimethyl-3-phenyl-4-{4-[2-(pyrrolidin-1-yl)ethoxy]phenyl}chromane or a salt thereof.

It has surprisingly been found that the compound of formula III can be obtained directly in a purity of more than 99% ee (enantiomeric excess) without further crystallization and that a stereoselective rearrangement of the (–)-3,4-cis enantiomer to the corresponding (–)-3,4-trans enatiomer of formula I is possible without any loss of chiral purity.

By the process disclosed in U.S. Pat. No. 4,447,622 the (–)-3,4-trans enantiomer is only obtained in a chiral purity above 80% ee by crystallization several times.

Also the yield of (–)-3,4-trans enantiomer obtained by the process of the invention is much better than the yield obtained by the already known process.

The process of the invention is shown in the following scheme 1:

Scheme 1

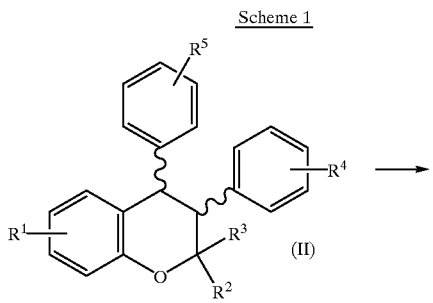

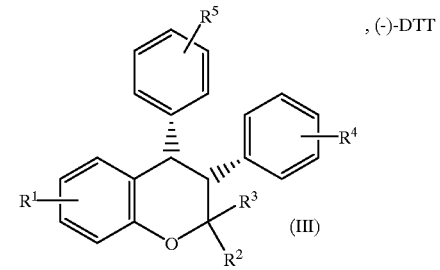

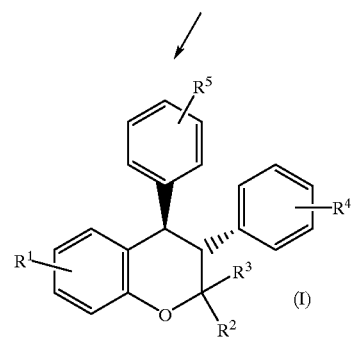

wherein $R^1$, $R^2$, $R^3$, $R^4$ and $R^5$ are as defined above.

In the first step the cis-racemate of formula II is reacted with a chiral acid like e.g. tartaric acid, lactic acid, mandelic acid, dibenzoyl tartaric acid camphorsulphonic acid or (–)-di-p-toluoyltartaric acid in an inert organic solvent. (–)-Di-p-toluoyltartaric acid is the preferred chiral acid. The resulting optically active acid salt of the (–)-3,4-cis enantiomer of formula III crystallizes from the reaction mixture by cooling.

As the inert organic solvent any such solvent which is not attacked by the conditions may be used for example a $C_{1-6}$-alkanol or mixtures thereof with water, tetrahydrofuran, acetone or acetonitril. It is preferred to use a $C_{1-6}$-alkanol as the organic solvent e.g. methanol, ethanol or propanol.

In the second step of the procedure the optically active salt of the (–)-3,4-cis enantiomer is firstly hydrolyzed to obtain the (–)-3,4-cis enantiomer which is then rearranged to the (–)-3,4-trans enantiomer by treatment with a strong base in an aprotic solvent. The treatment with the strong base is normally carried out by heating the mixture, preferably at 80–110° C.

It is not necessary to isolate the (–)-3,4-cis enantiomer before the rearrangement. The treatment with the strong base can be carried out directly in the organic phase resulting from the hydrolysis. The desired enantiomer may be isolated as a salt thereof.

As hydrolyzing agent is normally used a weak base as e.g. aqueous ammonia, sodium carbonate, potassium carbonate or the like.

As strong bases for the rearrangement may be used potassium hydroxide, sodium hydroxide, metal alkoxides, such as sodium methoxide, sodium ethoxide or potassium t-butoxide, sodium hydride, alkyllithiums such as n-butyllithium and sec-butyllithium; methal amides, such as sodium amide, magnesium diisopropylamide and lithium diisopropylamide or the like. The preferred strong bases are potassium hydroxide and potassium t-butoxide. The most preferred strong base is potassium t-butoxide.

The preferred aprotic solvents are dimethylsulfoxide, dimethylformamide, N-methylpyrrolidone (NMP) and toluene or combinations thereof. The combination NMP toluene and toluene DMSO is the preferred.

It is preferred to replace part of the chiral acid, e.g. (−)-di-p-toluoyltartaric acid, with a weak organic acid such as formic acid or fumaric acid in order to obtain a more economical process and a better separation.

As organic acid can be used e.g. formic acid, fumaric acid, methanesulfonic acid or the like. Formic acid is preferred.

Preferred compounds prepared by the process according to the invention include those in which $R^1$ is hydroxy or $C_{1-6}$alkoxy, especially methoxy. Furthermore, $R^2$ and $R^3$ preferably are the same and $C_{1-6}$alkyl, especially methyl; $R^4$ is preferably hydrogen; and $R^5$ is preferably—O—(CH$_2$)$_n$—NR$^6$R$^7$ wherein n is 2 and $R^6$ and $R^7$ together with the N atom is a saturated or unsaturated 5- or 6- membered heterocyclic group containing one or two heteroatom(s) and optionally substituted with $C_{1-6}$alkyl. Within particularly preferred embodiments, $R^1$ is in the 7-position and is hydroxy or $C_{1-6}$alkoxy, particularly methoxy; each of $R^2$ and $R^3$ is methyl, $R^4$ is hydrogen, and $R^5$ is in the 4-position and is 2-(pyrrolidin-1-yl)ethoxy.

A preferred embodiment of the invention provides a process for the preparation of (−)-3R, 4R-trans-7-methoxy-2,2-dimethyl-3-phenyl-4-{4-[2-(pyrrolidin-1-yl)ethoxy]phenyl}chromane, herein referred to as levormeloxifene, or a salt, thereof prepared from 3,4-cis-7-methoxy-2,2-dimethyl-3-phenyl-4-{4-[2-(pyrrolidin-1-yl)ethoxy]phenyl}chromane or a salt thereof, as shown in the following scheme 2.

Scheme 2

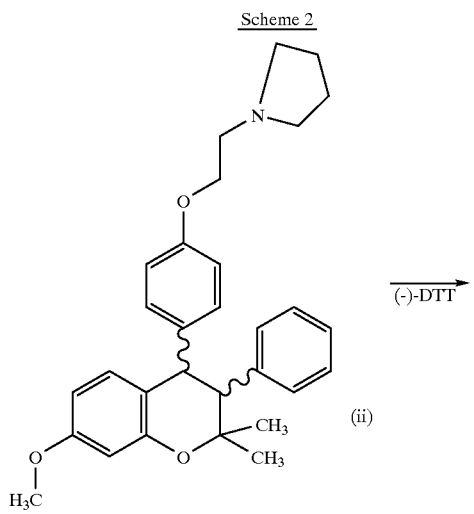

-continued

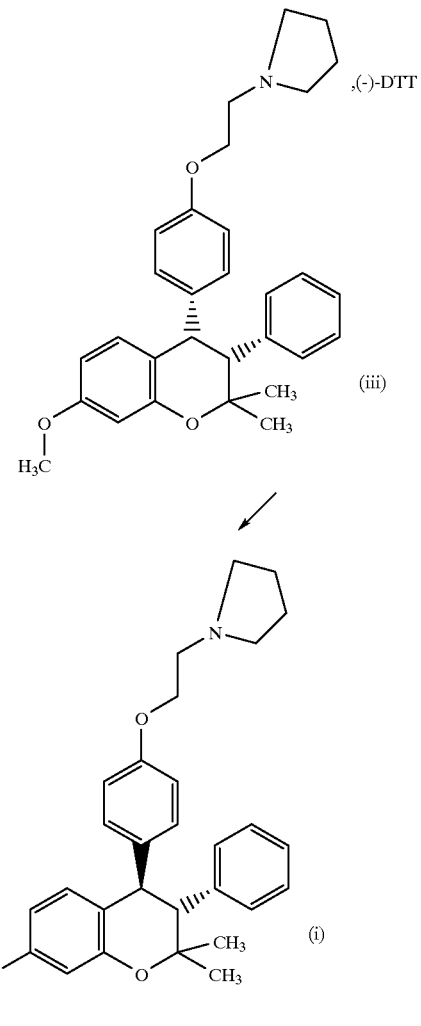

In sceme 1 and 2 above the compounds of formula III and formula (iii) are shown as the (−)-di-p-toluoyltartaric acid salt for the purpose of illustration only. However, the invention is by no means limited thereto, but is intended to comprise any chiral acid salt of the (−)-3,4-cis enantiomer.

In a particularly preferred embodiment the (−)-3R,4R-trans-7-methoxy-2,2-dimethyl-3-phenyl-4-{4-[2-(pyrrolidin-1-yl)ethoxy]phenyl}chromane is isolated as the hydrogen fumarate salt.

For the preparation of (−)-3R,4R-trans-7-methoxy-2,2-dimethyl-3-phenyl-4-{4-[2 -(pyrrolidin-1-yl)ethoxy]phenyl}chromane the preferred solvent for the reaction with (−)-di-p-toluoyltartaric acid is methanol.

In a further preferred embodiment the invention provides a process for the preparation of (−)-3,4-trans-2,2-dimethyl- 3-phenyl-4-{4-[2-(pyrrolidin-1-yl)ethoxy}phenyl-7-hydroxychroman.

As used herein, the term "$C_{1-6}$alkanol" includes methanol, ethanol, propanol, isopropanol, butanol, and the like.

As used herein, the term "$C_{1-6}$alkyl" includes straight and branched chain alkyl radicals containing from 1 to 6 carbon atoms, such as methyl, ethyl, n-propyl, isopropyl, n-butyl, tert-butyl, n-amyl, sec-amyl, n-hexyl, 2-ethylbutyl, 2,3-dimethylbutyl and the like.

The term "$C_{1-6}$alkoxy" includes straight and branched chain alkoxy radicals containing from 1 to 6 carbon atoms, such as methoxy, ethoxy, n-propoxy, isopropoxy, n-butoxy, tert-butoxy, n-amyloxy, sec-amyloxy, n-hexyloxy, 2-ethylbutoxy, 2,3-dimethylbutoxy and the like. "Halogen" includes chloro, fluoro, bromo and iodo. Herein, the term "5- or 6- membered heterocyclic group containing one or two hetero atom(s)" include groups wherein the heteroatom(s) preferably are selected among N, O, or S such as e.g., piperidine, pyrrolidine, N-methylpiperazine or morpholine.

Within the present invention, 3,4-diarylchromans of formula I may be prepared in the form of salts thereof e.g. pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. The acid addition salts may be obtained from the free base in a suitable solvent containing the appropriate acid, and the salt isolated by evaporating the solvent or otherwise separating the salt and solvent e.g. by crystallisation.

The starting compound for the process, the cis-racemate of formula II may be prepared according to known methods, such as those disclosed in U.S. Pat. No. 3,340,276 to Carney et al., U.S. Pat. No. 3,822,287 to Bolger, and Ray et al., *J Med Chem* 19 (1976), 276–279, the contents of which are incorporated herein by reference. The compound of formula II might also be prepared by hydrogenation of the corresponding chromene using e.g. palladium on carbon following the scheme:

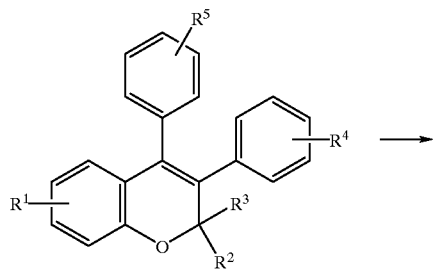

(II)

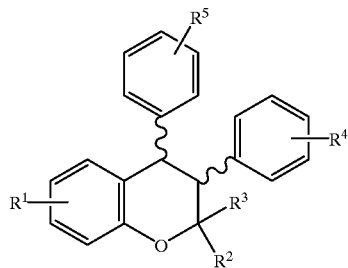

In connection with the process of the invention it has been found that it is possible to oxidize the (+)-cis-enantiomer left over from the crystallization in the first step of the process of the invention to the corresponding chromene. This is an additional advantage of the process of the invention by further reducing the cost of manufacture and providing an overall higher yield. The oxidation may be carried out with a quinone in an inert solvent as e.g. xylene, 1-butanol, propylen glycol or ethylen glycol and in presence of an organic acid as e.g. acetic acid or inorganic acid as e.g. hydrochloric acid and a supplementary oxidizing agent as e.g. sulfur. It is preferred to use chloranil as oxidizing agent, hydrochloride acid as inorganic acids and ethylen glycol as solvent.

According to the invention the optically active acid is preferably (−)-di-p-toluoyltartaric acid. This acid is much cheaper than the (+)-di-p-toluoyltartaric acid used in the process described in U.S. Pat. No. 4,447,662. This also makes the process of the invention more economic over the known process.

The process of the invention is described in greater detail in the following non-limitative examples.

EXAMPLE 1 cis-7-Methoxy-2.2-dimethyl-3-phenyl-4-{4-[2-(pyrrolidin-1-yl)ethoxy]phenyl}chromane 7-Methoxy-2,2-dimethyl-3-phenyl-4-{4-[2-(pyrrolidin-1-yl)ethoxy]phenyl}-3-chromene (25 g) was dissolved in acetic acid (250 ml) at 60° C. Palladium on carbon (2.5 g, 10%, 50% wet) was added and the mixture hydrogenated at 1 atmosphere hydrogen pressure at 60° C. for 24 hours. The catalyst was filtered off and the filtrate evaporated to en oil. The oil was dissolved in toluene (100 ml) and washed with sodium hydroxide solution (4M) until alkaline. The aqueous phase was separated and extracted with another portion of toluene (20 ml). The combined organic phases was washed with water (2×50 ml) and evaporated to an oil. The oil was dissolved in methanol (100 ml) and crystallized by adding water (200 ml). The product was filtered off and dried.

Yield 28 g (98%), m.p. 118–119° C. The identity of the product was verified by $^1$H-NMR and elemental analysis.

EXAMPLE 2

(−)-cis-7-Methoxy-2,2-dimethyl-3-phenyl-4-{4-[2-(pyrrolidin-1-yl)ethoxy]phenyl}chromane(−)-O,O'-ditoluoyltartrate cis-7-Methoxy-2,2-dimethyl-3-phenyl-4-{4-[2-(pyrrolidin-1-yl)ethoxy]phenyl}chromane (109 g) was dissolved in methanol (2 l) at 50° C. (−)-O,O'-ditoluoyltartrate acid (54,1 g) was added and then formic acid (6.8 ml). The solution was slowly cooled down to 32° C. and seeded. The product crystallized slowly overnight at ambient temperature. The mixture was cooled down to 0° C. for 4 hours and filtered off and washed with methanol (230 ml).

The enantiomeric purity was determined by Chiral HPLC to be better than 99%. Chiral HPLC system: Column: Chiradex 5, 250×4 mm(Merck). Eluent: 30% methanol/buffer (1% triethylammonium acetate, pH=4.1).

Yield 69 g (78%), m.p. 138–139° C. The structure of the compound was verified by $^1$H-NMR and elemental analysis. The composition of the salt is 4:3 i.e. four moles of base to three moles of ditoluoyl tartaric acid.

Optical rotation of the free base, $[\alpha]D^{20}=-51.3°$(c=1% in abs. ethanol).

EXAMPLE 3

(−)-trans-7-Methoxy-2,2-dimethyl-3-phenyl-4-{4-[2-(pyrrolidin-1-yl)ethoxy]phenyl}chromane hydrogenfumarate (−)-cis-7-Methoxy-2,2-dimethyl-3-phenyl-4-{4-[2-(pyrrolidin-1-yl)ethoxy]phenyl}chromane (−)-O,O'-ditoluoyltartrate (66.3 g) was suspended in a mixture of toluene (330 ml), water (265 ml) and sodium carbonate (20.8 g). The mixture was stirred until all salts have dissolved. The aqueous phase was separated and extracted with another portion of toluene (65 ml). The combined organic phase was washed with water (3×130 ml). The organic phase was dried by removal of water in an azeotropic distillation. To the dry toluene solution was added dimethylsulfoxide (66 ml) and finely grinded potassium hydroxide (15.4 g). The mixture was heated to reflux while water was distilled from the mixture. The reflux was maintained for 6 hours. The reaction mixture was cooled down to room temperature, water (200 ml) was added and the mixture stirred until all the salt was dissolved. The aqueous phase was separated and extracted with another portion of toluene (135 ml). The organic phases were pooled washed with water (2×200 ml) and evaporated to an oil. The oil was dissolved in ethanol (135 ml) at 40° C. and mixed with a solution of fumaric acid (9.1 g) in ethanol (265 ml) at 40–60° C. The mixture was stirred for 2 hours at ambient temperature and then for 1 hour at 0° C. The crystals were filtered off and dried. By Chiral HPLC the enantiomeric purity was determined to be better than 99.5% and the identity to be hydrogen fumarate salt of levormeloxifene, i.e. the minus enantiomer of the racemic compound Centchroman. Chiral HPLC system: Column: Chiradex5, 250×4 mm(Merck). Eluent: 70% methanol/buffer (0.25% triethylammonium acetate, pH=5.2).

Yield 43 g (85%), m.p. 220° C. with slight decomposition. The structure of the compound was verified by $^1$H-NMR and elemental analysis.

EXAMPLE 4

7-Methoxy-2,2-dimethyl-3-phenyl-4-{4-[2-(pyrrolidin-1-yl)ethoxy]phenyl}-3-chromene The filtrate from the crystallization of (−)-cis-7-methoxy-2,2-dimethyl-3-phenyl-4-{4-[2-pyrrolidin-1-yl)ethoxy] phenyl}chromane (−)-O,O'-ditoluoyltartrate was evaporated to an oil. that was dissolved in a mixture of toluene (300 ml), water ( 300 ml) and sodium hydroxide 4M, 200 ml). The aqueous phase was separated and extracted with another portion of toluene (100 ml). The combined toluene phase was washed with water and evaporated to an oil (73 g) which solidified on standing. A sample (1 g) of this solid was dissolved in xylene (20 ml, mixture of isomers). Acetic acid (1 ml), chloranil (0.5 g) and sulfur (0.5 g) was added and the mixture refluxed overnight. Water (50 ml) and sodium hydroxide (4M, 20 ml) was added and then sodium dithionite ( 2 g). The mixture was stirred for 5 hours. The aqueous phase was separated and the organic phase chromatographed through a short silica column with methanol as eluent. The fractions containing the product was combined. Concentrated hydrochloric acid ( 2 ml) was added and the solution was evaporated to dryness.

Yield 0.9 g (90%), m.p. 219° C., turns brown from 180–190° C. The identity of the product was verified by $^1$H-NMR and elemental analysis.

EXAMPLE 5

7-Methoxy-2,2-dimethyl-3-phenyl-4-{4-[2-(pyrrolidin-1-yl)ethoxy]phenyl}-3-chromene A mixture of (+)- and (−) -levormeloxifene (670 g), the filtrates from resolution of racemic cis-7-Methoxy-2,2-dimethyl-3-phenyl-4-{4-[2-(pyrrolidin- 1-yl)ethoxy] phenyl}chromane was dissolved in toluene (3 l). Conc. hydrochloric acid (0.21 l) was added and the mixture dried by an azeotropic distillation. The hydrochloride crystallises, after seeding, from the toluene solution when dry. The mixture was cooled down to 20° C. and the product filtered off and dried. Yield 650 g, 90%.

The product (650 g) and chloranil (434 g) was dissolved in ethylene glycol (3,6 l). The solution was heated at 90–125° C. until completion. For 3 hours at 125° C and 72 hours at 90° C. The mixture was cooled down to 20–30° C. and toluene (8 l) and sodium hydroxide (1.06 l, 36%) was added. The mixture was stirred for 10 minutes and the organic phase was separated off. Conc. hydrochloric acid (0.36 l) was added to the organic phase and a mixture of water-ethylene glycol-toluene was distilled from the solution until the distillation temperature reached 100° C. in the still head. The mixture was seeded while the mixture was still boiling. The mixture was cooled down to 20–30° C. and the product filtered off and washed with toluene (3 times 400 ml) and dried. Yield 670 g, 93%.

The product was purified further by a crystallisation of the base from ethanol - water. The product (670 g) was dissolved in a mixture of ethanol (2.66 l) and water (0.7 l) by heating to 60° C. A solution of sodium hydroxide (121 ml, 36%) was added. The solution was seeded while the mixture was 50–60° C. The mixture was cooled down to ca. 10° C. and the product filtered off and washed with 75% ethanol (3 times 300 ml) and dried. Yield 520 g, 79%.

EXAMPLE 6 cis-7-Methoxy-2,2-dimethyl-3-phenyl-4-{4-[2-(pyrrolidin-1-yl)ethoxy]phenyl}chromane.

7-Methoxy-2,2-dimethyl-3-phenyl-4-{4-[2-(pyrrolidin-1-yl)ethoxy]phenyl}-3-chromene (1 kg) was dissolved in acetic acid (10 l) by heating to 60° C. Palladium on carbon (10%, 50% wet, 100 g) was added and the mixture hydrogenated at 60° C., 2–3 atmospheres hydrogen pressure for 24 hours. The mixture was cooled down to 40–50° C. and the catalyst filtered off. The filtrate was evaporated in vacuum to an oil. It was dissolved in 2-propanol (4 l) and sodium hydroxide was added (ca. 1.2 l, 36%) in order to adjust the pH of the mixture to 10–11. The solution was seeded at 40–50° C. The mixture was cooled down to ca. 5° C. and the product filtered off and washed with water (3 l) and dried at 50° C. Yield 0.9 kg, 95%.

EXAMPLE 7

(−)-trans-7-Methoxy-2,2-dimethyl-3-phenyl-4-{4-[2-(pyrrolidin-1-yl)ethoxy]phenyl}chromane hydrogen fumararate (−)-cis-7-Methoxy-2,2-dimethyl-3-phenyl-4-{4-[2-(pyrrolidin-1-yl)ethoxy]phenyl}chromane (−)—O,O'-ditoluoyltartrate (15.4 g) was suspended in a mixture of toluene (77 ml), water (62 ml) and sodium carbonate (4.8 g). The mixture was stirred until all salts have dissolved. The aqueous phase was separated and extracted with another portion of toluene (20 ml). The combined organic phase was washed with water (3×20 ml). The organic phase was evaporated to an oil (9.3 g). The oil was dissolved in N-methylpyrrolidone (3.3 ml) and toluene (80 ml). Potassium tert-butoxide (1.2 g) was added and the mixture was heated to reflux while water was distilled from the mixture. The reflux was maintained for 6 hours. The reaction mixture was cooled down to room temperature, water ( 45 ml) was added and the mixture stirred until all the salt was dissolved. The aqueous phase was separated and extracted with another portion of toluene (40 ml). The organic phases were pooled washed with water (2×50 ml) and evaporated to an oil. The oil was dissolved in ethanol (16 ml) at 40° C. and mixed with a suspension of fumaric acid (4.2 g) in ethanol (31 ml) at 60° C. The mixture was stirred. Additional ethanol (47 ml) was added and the mixture was refluxed for 3 hours. The mixture was stirred at ambient temperature overnight. The crystals were filtered off and dried.

Yield 9.9 g (85%), m.p. 220–220° C. with slight decomposition. The structure of the compound was verified by $^1$H-NMR and elemental analysis.

I claim:

1. A process for the preparation of (−)-3,4-trans-compounds of the following formula I

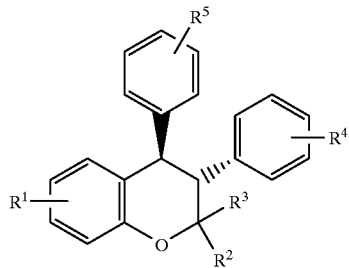

(I)

wherein $R^1$, $R^4$ and $R^5$ are individually hydrogen, hydroxy, halogen, trifluoromethyl, $C_{1-6}$alkyl, $C_{1-6}$alkoxy or —O—$(CH_2)_n$—$NR^6R^7$ wherein n is an integer in the range of 1 to 6 and $R^6$ and $R^7$ independently are $C_{1-6}$alkyl or $R^6$ and $R^7$ together with the N atom is a saturated or unsaturated 5- or 6- membered heterocyclic group containing one or two heteroatom(s) which heterocyclic group is optionally substituted with $C_{1-6}$alkyl; and $R^2$ and $R^3$ are individually hydrogen or $C_{1-6}$alkyl; or a salt thereof, which comprises treating a cis-racemate of a compound of formula II

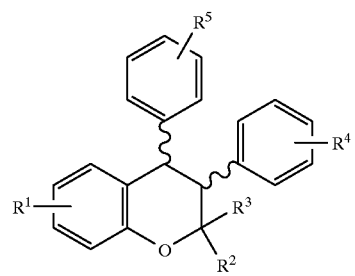

(II)

wherein $R^1$, $R^2$, $R^3$, $R^4$ and $R^5$ are as defined above or a salt thereof with a chiral acid in an inert organic solvent, crystallizing the chiral acid salt of the (−)-3,4-cis enantiomer, hydrolyzing the optically active acid salt and rearranging the resulting (−)-3,4-cis enantiomer to the corresponding (−)-3,4-trans enantiomer of above formula I by treatment with a strong base in an aprotic solvent and optionally forming a salt thereof.

2. A process according to claim 1, wherein $R^1$ is hydroxy or $C_{1-6}$alkoxy, $R^2$ and $R^3$ are the same and are $C_{1-6}$alkyl, $R^4$ is hydrogen and $R^5$ is —O—$(CH_2)_n$—$NR^6R^7$ wherein n is 2 and $R^6$ and $R^7$ together with the N atom is a saturated or unsaturated 5- or 6- membered heterocyclic group containing one or two heteroatom(s) and optionally substituted with $C_{1-6}$alkyl.

3. A process according to claim 1 wherein $R^1$ is in the 7-position and $R^5$ is in the 4-position.

4. A process according to claim 1 wherein $R^1$ is methoxy.

5. A process according to claim 1 wherein $R^1$ is hydroxy.

6. A process according to claim 1 wherein $R^2$ is methyl.

7. A process according to claim 1 wherein $R^3$ is methyl.

8. A process according to claim 1 wherein $R^4$ is hydrogen.

9. A process according to claim 1 wherein $R^5$ is pyrrolidinoethoxy.

10. A process according to claim 1, wherein (−)-3R,4R-trans-7-methoxy-2,2-dimethyl-3-phenyl-4-{4-[2-(pyrrolidin-1-yl)ethoxy]phenyl}chromane or a salt thereof is prepared from 3,4-cis-7-methoxy-2,2-dimethyl-3-phenyl-4-{4-[2-(pyrrolidin-1-yl)ethoxy]phenyl}chromane or a salt thereof.

11. A process according to claim 10 wherein (−)-3R,4R-trans-7-methoxy-2,2-dimethyl-3-phenyl-4-{4-[2-(pyrrolidin-1-yl)ethoxy]phenyl}chromane is isolated as the hydrogen fumarate salt.

12. A process according to claim 1, wherein the reaction with the chiral acid is carried out in an $C_{1-6}$alkanol or mixtures thereof with water, tetrahydrofuran, acetone or acetonitril.

13. A process according to claim 1 wherein the chiral acid is (−)-di-p-toluoyltartaric acid.

14. A process according to claim 13, wherein the reaction with the (−)-di-p-toluoyltartaric acid is carried out in an $C_{1-6}$alkanol.

15. A process according to claim 14, wherein the reaction with the (−)-di-p-toluoyltartaric acid is carried out in methanol.

16. A process according to claim 1 wherein the rearrangement of the (−)-3,4-cis enantiomer to the (−)-3,4-trans enantiomer is carried out with potassium hydroxide in dimethylsulfoxide and toluene.

17. A process according to claim 1 wherein the rearrangement of the (−)-3,4-cis enantiomer to the (−)-3,4-trans enantiomer is carried out with potassium t-butoxide in N-methylpyrrolidine and toluene.

18. A process according to claim 1 wherein the cis-racemate of formula II is obtained by hydrogenation of the corresponding 3-chromene.

19. A process according to claim 18 wherein the 3-chromene is obtained by oxidation of the corresponding (+)-3,4-cis-chromane.

20. A process according to claim 19 wherein the oxidation is carried out with chloranil and sulphur in xylene in the presence of acetic acid.

21. A process according to claim 19 wherein the oxidation is carried out with chloranil in ethylenglycol on the hydrochloride of the cis-chromane.

* * * * *

UNITED STATES PATENT AND TRADEMARK OFFICE
CERTIFICATE OF CORRECTION

PATENT NO.    :    5,925,771

DATED    :    July 20, 1999

INVENTOR(S)    :    Svend Treppendahl

It is certified that error appears in the above-identified patent and that said Letters Patent is hereby corrected as shown below:

Col. 15, line 6, claim 19. Claim 19 is dependent on Claim 1.

Signed and Sealed this

Eighth Day of February, 2000

Q. TODD DICKINSON

*Attest:*

*Attesting Officer*    *Commissioner of Patents and Trademarks*